United States Patent
Frank et al.

(10) Patent No.: US 11,604,556 B2
(45) Date of Patent: *Mar. 14, 2023

(54) GRAPHICAL USER INTERFACE FOR MARKING ANATOMIC STRUCTURES

(71) Applicant: CENTERLINE BIOMEDICAL, INC., Cleveland, OH (US)

(72) Inventors: Richard C. Frank, Newtonville, MA (US); Simon Pogrebinsky, Natick, MA (US)

(73) Assignee: CENTERLINE BIOMEDICAL, INC., Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/478,472

(22) Filed: Sep. 17, 2021

(65) Prior Publication Data

US 2022/0004305 A1 Jan. 6, 2022

Related U.S. Application Data

(63) Continuation of application No. 16/265,762, filed on Feb. 1, 2019, now Pat. No. 11,150,776.

(Continued)

(51) Int. Cl.
  *G06F 3/04812* (2022.01)
  *G06F 3/04842* (2022.01)
  (Continued)

(52) U.S. Cl.
  CPC .......... *G06F 3/04812* (2013.01); *A61B 34/25* (2016.02); *A61B 90/37* (2016.02);
  (Continued)

(58) Field of Classification Search
  None
  See application file for complete search history.

(56) References Cited

U.S. PATENT DOCUMENTS 5,825,001 A 10/1998 Oba et al.
6,533,455 B2 3/2003 Graumann et al.
(Continued)

FOREIGN PATENT DOCUMENTS

EP 1421913 A1 5/2004
JP 2007185278 A 7/2007
(Continued)

OTHER PUBLICATIONS

Datacomppolska, "BIM Vision—Cutting and cross-section options," Aug. 21, 2017, https://www.youtube.com/watch?v=elB6pzZztxU.
(Continued)

*Primary Examiner* — Ryan Barrett
(74) *Attorney, Agent, or Firm* — Tarolli, Sundheim, Covell & Tummino LLP

(57) ABSTRACT

In an example, a graphical user interface can be used to display a graphical representation of a virtual reference structure for an anatomic structure, the reference structure being determined from geometry of the anatomic structure. A location parameter along the reference structure is determined in response to a first user input from a user input device. A graphical proxy marker is displayed on the graphical representation of the reference structure based on the location parameter. A fixed location is selected along the reference structure for a final graphical marker in response to a second user input from the from the user input device. An output visualization is generated to include at least one view of the anatomic structure and a graphical representation of the final graphical marker at the fixed location.

17 Claims, 7 Drawing Sheets

Related U.S. Application Data

(60) Provisional application No. 62/625,377, filed on Feb. 2, 2018.

(51) Int. Cl.
*A61B 34/00* (2016.01)
*A61B 90/00* (2016.01)
*A61B 34/20* (2016.01)
*A61B 34/10* (2016.01)

(52) U.S. Cl.
CPC .... *G06F 3/04842* (2013.01); *A61B 2034/105* (2016.02); *A61B 2034/107* (2016.02); *A61B 2034/2068* (2016.02)

(56) References Cited

U.S. PATENT DOCUMENTS

| | | |
|---|---|---|
| 7,010,095 B2 | 3/2006 | Mitschke et al. |
| 7,556,428 B2 | 7/2009 | Sukovic et al. |
| 7,671,887 B2 | 3/2010 | Pescatore et al. |
| 7,824,328 B2 | 11/2010 | Gattani et al. |
| 8,060,185 B2 | 11/2011 | Hunter et al. |
| 8,213,693 B1 | 7/2012 | Li |
| 8,219,179 B2 | 7/2012 | Ganatra et al. |
| 8,224,632 B2 | 7/2012 | Whirley et al. |
| 8,238,625 B2 | 8/2012 | Strommer et al. |
| 8,248,413 B2 | 8/2012 | Gattani et al. |
| 8,301,226 B2 | 10/2012 | Csavoy et al. |
| 8,315,355 B2 | 11/2012 | Mohamed |
| 8,442,618 B2 | 5/2013 | Strommer et al. |
| 8,467,853 B2 | 6/2013 | Hunter et al. |
| 8,612,890 B2 | 12/2013 | Nijlunsing et al. |
| 9,195,801 B1 | 11/2015 | Sankaran et al. |
| 9,401,047 B2 | 7/2016 | Bogoni et al. |
| 2003/0011624 A1 | 1/2003 | Ellis |
| 2004/0249270 A1 | 12/2004 | Kondo et al. |
| 2005/0041042 A1 | 2/2005 | Rajarajan et al. |
| 2006/0058647 A1 | 3/2006 | Strommer et al. |
| 2008/0020362 A1 | 1/2008 | Cotin et al. |
| 2009/0227861 A1 | 9/2009 | Ganatra et al. |
| 2010/0210938 A1 | 8/2010 | Verard |
| 2010/0312094 A1 | 12/2010 | Guttman et al. |
| 2011/0054300 A1 | 3/2011 | Yamamoto et al. |
| 2011/0166446 A1 | 7/2011 | Whitmore, III et al. |
| 2011/0295109 A1 | 12/2011 | Lavallee et al. |
| 2012/0105436 A1 | 5/2012 | Averbuch |
| 2013/0079628 A1 | 3/2013 | Groszmann |
| 2016/0135787 A1 | 5/2016 | Anderson et al. |
| 2017/0319172 A1 | 11/2017 | Harlev et al. |
| 2017/0325891 A1 | 11/2017 | Harlev et al. |

FOREIGN PATENT DOCUMENTS

| | | |
|---|---|---|
| JP | 2008061858 A | 3/2008 |
| JP | 2008136850 A | 6/2008 |
| JP | 2009072317 A | 4/2009 |
| JP | 2012529352 A | 11/2012 |
| WO | 2008035271 A2 | 3/2008 |
| WO | 2008107905 A2 | 9/2008 |
| WO | 2010074986 A1 | 7/2010 |
| WO | 2010086374 A1 | 8/2010 |
| WO | 2012127353 A1 | 9/2012 |
| WO | 2012143290 A1 | 10/2012 |
| WO | 2014151651 A1 | 9/2014 |
| WO | 2016082018 A1 | 6/2016 |
| WO | 2017030913 A2 | 2/2017 |

OTHER PUBLICATIONS

Applicant: Centerline Biomedical, Inc.; International Search Report and Written Opinion; International PCT Application No. PCT/US2019/016360; Filing Date: Feb. 1, 2019; 7 pgs.

Applicant: Centerline Biomedical, Inc.; "Graphical User Interface for Marking Anatomic Structures"; European Patent Application No. 19747446; Extended European Search Report; dated Sep. 6, 2021; 18 pgs.

Applicant: Centerline Biomedical, Inc.; "Graphical User Interface for Marking Anatomic Structures"; European Patent Application No. 19747446; European Office Action; dated Jul. 5, 2022; 6 pgs.

ated ANATOMIC STRUCTURES

GRAPHICAL USER INTERFACE FOR MARKING ANATOMIC STRUCTURES

CROSS-REFERENCE TO RELATED APPLICATION

This application is a continuation of U.S. Non-provisional patent application Ser. No. 16/265,272, filed 1 Feb. 2019, and entitled GRAPHICAL USER INTERFACE FOR MARKING ANATOMIC STRUCTURES, which claims the benefit of U.S. Provisional Patent Application No. 62/625,377, filed Feb. 2, 2018, and entitled OSTIA PLACEMENT TOOL, each of which applications is incorporated herein by reference in its entirety.

TECHNICAL FIELD

This disclosure relates to a graphical user interface for marking tubular anatomic structures in a visualization.

BACKGROUND

Various forms of image-guided surgical navigation systems have been developed. In some examples, such systems use medical imaging technologies to create a model of the anatomic region of interest for viewing during various phases of the procedure, including pre-planning and intra-operative phases. As an example, a surgeon uses special instruments, which are tracked by the navigation system. The position of the tracked instrument in relation to the patient's anatomy may be shown on images, including as the surgeon moves the instrument during a procedure.

SUMMARY

This disclosure relates to a graphical user interface for marking tubular anatomic structures in a visualization.

As one example, one or more non-transitory computer readable media have instructions stored thereon, for execution by a computer that includes a graphical user interface and a user input device. The instructions are programmed to perform a method that includes displaying a graphical representation of a virtual reference structure for an anatomic structure. The reference structure is determined from geometry of the anatomic structure. A location parameter along the reference structure is determined in response to a first user input from a user input device. A graphical proxy marker is displayed on the graphical representation of the reference structure based on the location parameter. A fixed location is selected along the reference structure for a final graphical marker in response to a second user input from the from the user input device. An output visualization is generated to include at least one view of the anatomic structure and a graphical representation of the final graphical marker at the fixed location.

As another example, a computer-implemented method for marking an anatomic structure includes displaying a graphical representation of a virtual reference structure for the anatomic structure on an output device, the reference structure being determined from geometry of the anatomic structure. The method also includes determining a location parameter with respect to the reference structure in response to a first user input from a user input device. The method also includes displaying a graphical proxy marker on the graphical representation of the reference structure based on the location parameter. The method also includes selecting a fixed location along the reference structure for a final graphical marker in response to a second user input from the from the user input device. The method also includes generating an output visualization that includes at least one view of the anatomic structure and a graphical representation of the final graphical marker at the fixed location.

DETAILED DESCRIPTION

Figure 1:
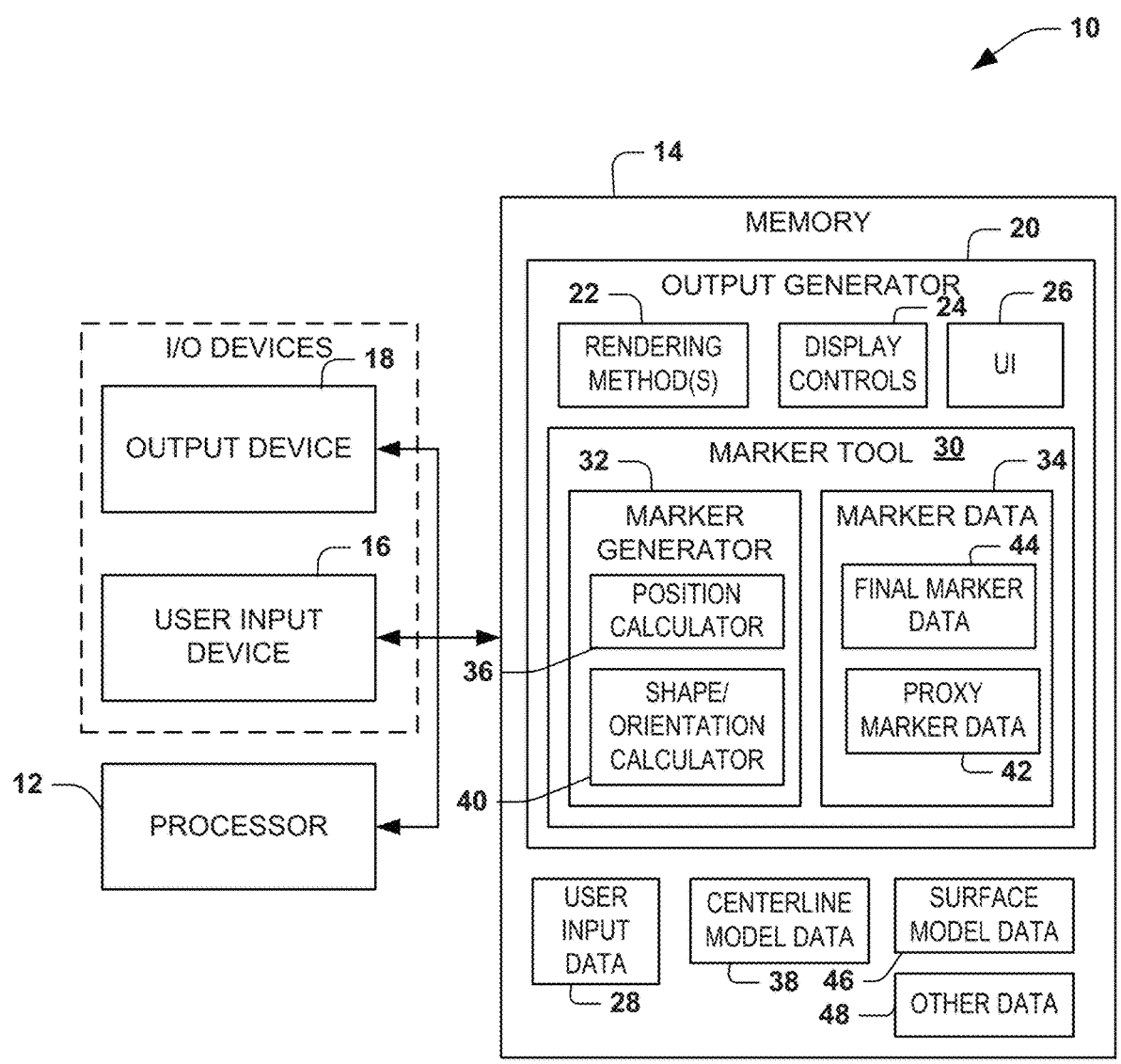
FIG. 1 is an example of a computer system programmed to implement a tool for marking anatomic structures.

This disclosure relates to graphical user interface for marking anatomic structures in a visualization.

The systems and methods disclosed herein may be used in a pre-operative planning stage and/or intra-operatively to place one or more graphical markers at selected locations with respect to a graphical representation of anatomy. Each graphical marker may be visualized on the display at a fixed user-selected location to provide a guidance (e.g., a way-point or target) that remains anatomically and geometrically consistent intra-operatively over a number of different views. For example, a ring-shaped graphical marker may be placed to designate an opening between adjacent fluidly connected anatomic structures, such as an ostium between two vessels (e.g., a main vessel and a branch vessel), an opening between an organ and a vessel, an opening between two chambers of an organ.

As an example, a graphical representation of a portion of a patient's anatomy can be visualized on an interactive display. A computer (or other processor-based apparatus) provides a graphical user interface on the display that is interactive in response to a user input received from one or more user input devices (e.g., a hardware interface, such as mouse, touch screen, keyboards, gesture interface or the like). To place a marker, a user activates the marker tool in a graphical or other user interface that includes a graphical representation of a virtual anatomic reference structure (e.g., a centerline of an anatomic lumen or an axis of symmetry for another anatomic structure). For example, user input instructions (from a user input device) position a pointer along the centerline that is visualized in a graphical user interface of the marker tool. A graphical proxy marker can be displayed at a current pointer location along the centerline (or other anatomic reference). The graphical proxy marker provides a temporary graphical visualization of the marker relative to the anatomic reference to allow the user to decide whether the location is satisfactory or if an alternative location would be more suitable. When a suitable location for the proxy marker is determined, the user can employ the user input device to select and fix the location of the marker with respect to the anatomic reference to define parameters for a graphical final marker. The selected location for this and any number of markers can be stored in memory, such as linked to a respective one of a plurality of points distributed along the length of the centerline.

The computer can generate an output visualization that is provided to the display to visualize a graphical representation of the anatomic structure that includes the graphical final marker. In some examples, an output generator can be programmed to utilize a graphics pipeline to render a number of different views of the anatomic structure, each including a visualization of the marker at a consistent anatomic location. Each view of the anatomic structure may be concurrently displayed (e.g., in different windows) or displayed at different times (e.g., in the same or different windows). Because the position of the graphical final marker is linked to a given point along the centerline (or other graphical structure) and the geometry of anatomy that marked is known, the final marker can retain a consistent and accurate relative position and size with respect to a patient's anatomy in each visualization. In this way, a surgeon or other user can place the marker to provide a waypoint (e.g., a luminal waypoint for vessel or other anatomic structure) along a path to a target site or identify the target site itself over a number of different views. For example, a ring-shaped graphical marker may be placed at an ostium of a blood vessel (e.g., the aorta) to designate the opening to a branch into which an instrument (e.g., catheter and/or guidewire) may be inserted as part of a procedure. In the context of intra-operative guidance, a graphical visualization of the catheter and/or guide wire may also be rendered in the output visualization along with the patient anatomy and the graphical marker, including during movement of the instrument along the anatomic lumen of the patient's body.

The approach herein affords a user flexibility in placing the graphical marker at a desired location to provide personalized guidance. In many example embodiments disclosed herein, the anatomic structures include tubular anatomic structures, such as one or more blood vessels (e.g., the aorta and its associated branching arteries. It is to be understood that the graphical user interface and methods are equally applicable to other anatomic tubular structures as well as to non-tubular structures, such as organs.

FIG. 1 depicts an example of a computer system 10 programmed for marking anatomic structures. The computer system 10 includes one or more processors 12 and associated memory 14. The memory 14 can include one or more non-transitory computer-readable media having instructions and data stored thereon. The system 10 also includes one or more input/output (I/O) devices demonstrated as a user input device 16 and an output device 18. For example, the user input device 16 may include a keyboard, mouse, touch screen interface, gesture interface or the like that is configured to provide instructions and commands that can be stored in the memory 14 as user input data 28. As an example, the user input device 16 can provide the input data 28 to specify a position (e.g., spatial coordinates) and/or movement of a pointer with respect to a displayed graphical representation in the output device 18. Additionally or alternatively, the user input device 16 can be configured to provide the input data 28 to select or activate a function at a given location (e.g., an area of the display) for which one or more functions are associated. The output device 18 can include one or more displays, such as a monitor, heads up display or virtual reality headset or goggles. Thus, in some examples, the user input device 16 and the output device 18 may be integrated to provide both inputs and outputs for the system 10.

As mentioned, the memory 14 includes instructions that can be executed by the processor 12 to perform various functions disclosed herein. In the example of FIG. 1, the instructions include an output generator 20 programmed to generate an interactive output visualization that can be rendered as a graphical output and displayed in the output device 18. The output generator 20 can include one or more rendering methods 22 for rendering various objects in the output visualization. The output generator 20 can also include display controls 24 programmed to set one or more visualizations parameters to control, for example, viewing angle, size, colors and the like in the output visualization that is provided by the rendering method 22. The output generator 20 can also include a user interface 26 to enable user interaction (e.g., through user input device 16) with the various functions of the output generator 20.

The output generator 20 also includes a marker tool 30 that is programmed to mark anatomic structures in response user input data 28 provided based on the user input device 16. The marker tool 30 includes the marker generator 32 that is programmed to generate one or more graphical markers that can be visualized relative to anatomic structures. For example, the marker generator 32 is programmed to generate marker data 34 that is utilized by the rendering methods 22 of the output generator 20 to display one or more graphical markers relative to an anatomic structure in response to a user input. The marker data 34 can include parameters to determine a position, size and other graphical attributes (e.g., color, brightness transparency) of the marker with respect to the anatomic structure where it is being placed.

By way of example, as part of executing the marker tool 30, the output generator 20 can render a graphical representation of a virtual anatomic reference. For instance, the anatomic reference can be a centerline of a tubular anatomic structure, such as a blood vessel (e.g., the aorta or other arteries, veins) or other tubular structures, such as the gastrointestinal tract, ureter or the like. The type of anatomic reference can be based on the shape of anatomic structure and how it is stored in memory (e.g., model data 38, 46).

The marker generator 32 can include a position calculator 36 programmed to determine one or more location parameters for a marker in response to the user input data 28. The location parameters can be stored as part of the marker data 34. The rendering method of output generator 20 employs the location parameter to control visualizing the graphical marker with respect to the anatomic reference in the displayed graphical representation. For example, the position calculator 36 can determine the location parameter according to a location of the pointer, as provided by user input data 28, with respect to predetermined spatial points distributed along the anatomic reference (e.g., the centerline).

As an example, the centerline is generated from a three-dimensional patient-specific implicit centerline model that is described in centerline model data 38 stored in the memory 14. The centerline model data 38 may include one or more parameters to describe a spline equation corresponding to a series of geometric knots in three-dimensional space. The rendering method 22 thus can be programmed to calculate spline control points from the geometric knots and evaluate the spline equation using the computed control points for a given parameter value, such that the centerline is a function of a single parameter. For example, the rendering method 22 can compute the centerline as a function of a single parameter (u) representing geometric knots that goes from zero to one and varies along a path corresponding to the axis of the tubular structure taken by selecting a spacing of the parameter u. The value can be computed at each respective spacing and the rendering method 22 can plot the curve as a series of corresponding line segments drawn in the output visualization between the values of the parameter u. For example, if a spacing of 0.1 is selected, the rendering method can evaluate the curve corresponding to the centerline at u=0, u=0.1, u=0.2, etc. and the corresponding points for each value of u can be connected to provide a plot corresponding to the centerline in the graphical output visualization in the output device 18.

The geometric knots distributed along the length of the centerline thus have a known position in the graphical visualization that is provided in the output device 18 as does the pointer based on the user input data 28. The position calculator 36 thus can determine a relative position of the pointer and geometric knots along the centerline based on the user input data 28 and centerline model data 38. For example, the position calculator 36 computes a distance between the pointer element and the geometric knots to, in turn, identify a closest geometric knot to the pointer based on the computed distance. For example, a user can hover the pointer over the length of the centerline in the output visualization and a closest geometric knot can be identified and stored as part of the marker data 34 as the user input data changes according to the movement of the pointer with respect to the centerline.

The marker generator 32 can provide the marker data 34 to include both proxy marker data 42 and final marker data 44. The proxy marker data 42 provides parameters for a graphical proxy marker to be displayed with respect to the anatomic reference structure. The graphical proxy marker and anatomic structure are utilized by the marker tool to identify and then select a fixed location for the final marker. Thus, the proxy marker data 42 can change according to the pointer position. For example, the rendering method can render the graphical proxy marker along the length of a centerline, based on the calculated position, as the pointer hovers over the graphical representation of the centerline in the visualization that is provided on the output device 18.

In some examples, the size, shape and orientation of the graphical proxy marker may remain fixed as the pointer of the user input device moves along the centerline (or other anatomic reference) to change the location parameter for the graphical proxy marker. As mentioned, the location parameter for the proxy marker may correspond to spatial coordinates of geometric knots determined by the rendering method based on the model data 38. The size, shape and orientation of the graphical marker can be stored in the marker data 34 (e.g., proxy marker data 42 or final marker data 44).

In other examples, the graphical marker can have a size, shape and/or orientation parameter that varies based on the location of the marker along the centerline. As such, the marker generator 32 includes a shape/orientation calculator 40 programmed to determine a shape, size and/or orientation of the marker that the rendering method 22 is to visualize on the output device 18. For example, the shape/orientation calculator 40 can dynamically determine a size of the graphical proxy marker of the geometric knots according to the radius of the tubular structure as provided by surface model data 46. For example, the surface model data 46 describes surface geometry of the structure tin three-dimensional space implicitly by a set of one equations and parameters derived from image data, as disclosed below. Thus, as the pointer of the user input device 16 moves along the centerline to change the location parameter, the size of the graphical proxy marker can reflect the size of the tubular anatomic structure.

Additionally or alternatively, the shape/orientation calculator 40 can dynamically determine an orientation of a graphical marker with respect to the position and direction of the centerline structure (as provided by centerline model data 38) at the position along the centerline where the marker is being rendered. For example, as the position of the graphical proxy marker is moved along the centerline (e.g., by moving the pointer of the user input device 16 along the centerline), the shape/orientation calculator 40 can determine an orientation of the proxy marker as to be substantially perpendicular to the direction of the centerline. For example, a virtual plane extending through the body of the graphical proxy marker (e.g., along orthogonal axes of the marker) can be maintained perpendicular to the centerline.

In some examples, the graphical proxy marker has a toroidal (e.g., ring-shaped) geometry having a center or centroid that is positioned along the curved centerline (e.g., co-located with the geometric knots of the centerline based on model data 38). The size of the toroidal shape of the graphical proxy marker may be fixed or it may vary according to the surface geometry of the tubular structure at the position where it is rendered along the centerline. Additionally or alternatively, the orientation of the toroidal shape of the graphical proxy marker may vary (e.g., be perpendicular) according the direction of the tubular structure at the position where it is rendered along the centerline.

The position, shape, size and orientation of graphical proxy marker can be stored in the proxy marker data 42 for use by the rendering method 22 in generating the visualization in the graphical output provided to the output device 18. By changing the position of the graphical proxy marker as the pointer moves along the centerline, the user is afforded a dynamic visualization to decide upon placement for the marker.

Once a user has decided to set the marker at a desired location along the length of the anatomic structure, a user can employ the user input device 16 to select the fixed location for a final graphical marker. For example, the user may utilize the user input device 16 to double click on (or near) the graphical proxy marker, activate a GUI button or select another user interface element to set a location that is stored in the user input data 28. The marker generator 32 in turn specifies the selected fixed location with respect to the anatomic structure and stores it as part of the final marker data 44. As an example, the location parameter for the final marker data 44 can correspond to a given geometric knot along the centerline, which may be added or linked to the centerline model data to specify the location along the centerline where the final graphical marker is to be rendered in the visualization.

Either automatically following configuring the final graphical marker or in response to a user input with the user input device 16, the marker tool may be closed from the GUI and the output generator 20 may enter a normal visualization/guidance mode. In the normal mode, the rendering method 22 can generate the output visualization to include one or more views of the anatomic structure, which also includes a graphical representation of the final marker based on final marker data 44 at the selected location. As a user input with the user input device may utilize the display controls 24 to change or add viewing angles, the graphical marker remains at the selected location relative to the anatomic structure based on the final marker data 44.

In some examples, the output generator 20 is also programmed to generate the graphical representation of an instrument, such as a catheter and/or guide wire that is inserted in the tubular structure. The location of the instrument (e.g., guide wire or catheter) can be provided based on tracking data for a sensor that is located on or fixed with respect to the guide wire and/or catheter. The location and graphical description of such instrument may be provided by other data 48 that is stored in the memory 14. For example, the other data 48 includes model data describing the geometry of the instrument as well as location information for the instrument based on the tracking data, which is variable and can change over time in response to the position of the instrument within the anatomic structure. The output generator 20 thus may generate an aggregate output visualization of the anatomic structure, such as based on the centerline model data 38 and the surface model data 46, a graphical marker based on the marker data 44 as well as the graphical representation of the instrument based on the other data 48. In this way, the position of the instrument can be visualized and tracked as it moves within the anatomic structure based on its relative position that changes with respect to time according to the relative position of the sensor within the anatomic structure. As disclosed herein, where the anatomic structure is a tubular structure including one or more blood vessels, the final graphical marker can specify the location and provide a visualization of an ostium.

Figure 2:
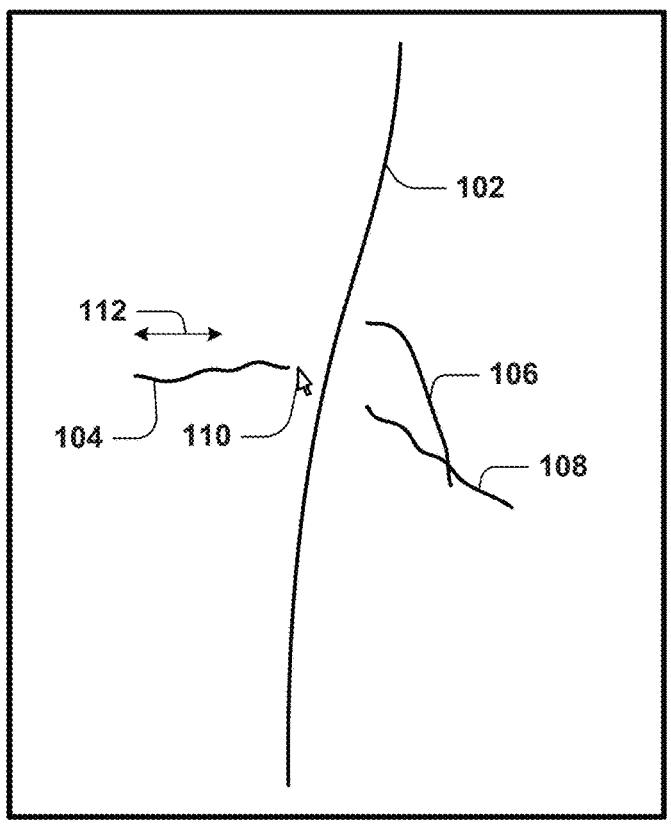
FIG. 2 depicts an example of a graphical user interface for placing a graphical marker with respect to a tubular anatomic structure.
Figure 3:
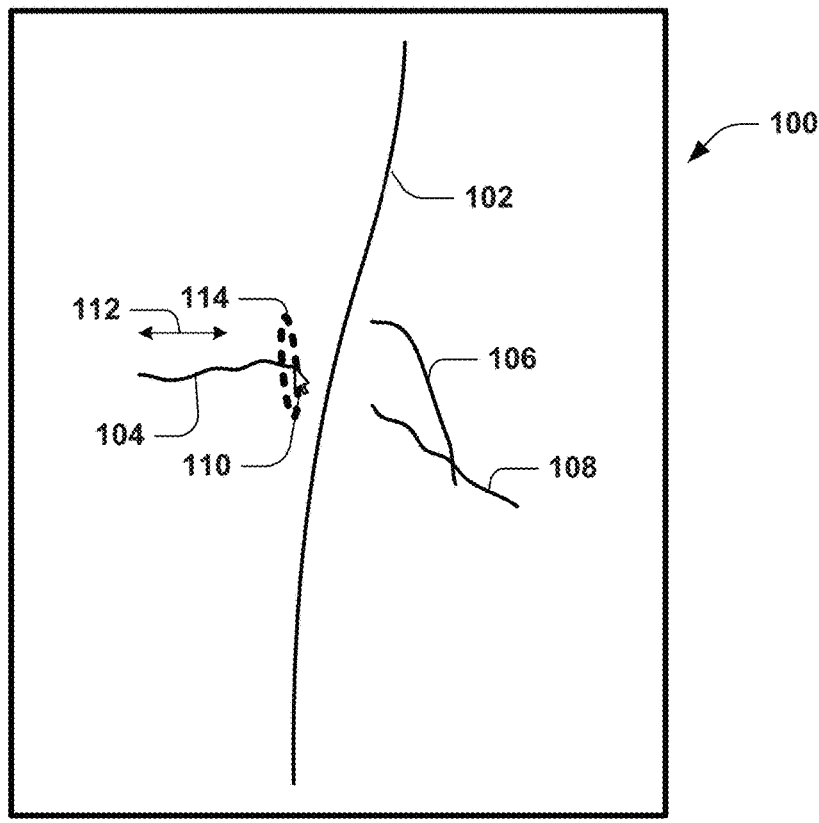
FIG. 3 depicts an example of the user interface of FIG. 2 showing a graphical proxy marker being placed relative to a centerline of an anatomic structure.
Figure 4:
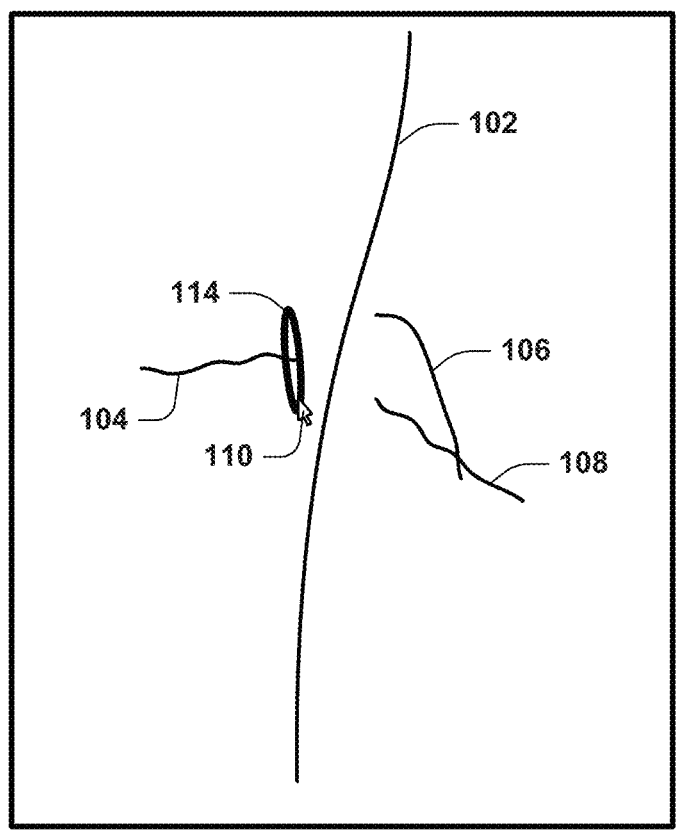
FIG. 4 depicts an example of the graphical user interface at FIG. 2 showing a location being selected for placement of a final graphical marker.

By way of further example, FIGS. 2, 3 and 4 depict examples of a graphical user interface demonstrating a process that can be implemented for setting a location for one or more graphical markers in response to a user input. The examples of FIGS. 2, 3 and 4 are illustrated in the context of an aorta that includes a plurality of branch arteries. It is understood that the approach disclosed herein for placing a marker can be applied to other blood vessels as well as to other shapes and sizes of anatomic structures. In the examples of FIGS. 2, 3 and 4, the graphical user interface 100 illustrates a patient-specific centerline for the descending aorta, demonstrated at 102, and other centerlines 104, 106, and 108 for branching arteries.

In the example of FIG. 2, a marker tool (e.g., tool 30) has been activated to provide the resulting graphical user interface 100 for placement of one or more graphical markers. A pointer 110 can be moved within the GUI 100 in response to the user input with a user input device (e.g., device 16) and stored as user input data (e.g., data 28). The pointer 110 could be moved along any of the centerlines 102, 104, 106 and 108 for marker placement (in response to a user input). In the following example, the pointer 110 will be moved along branch centerline 104 such as in the direction indicated at 112. As shown in FIG. 3, as the pointer 110 moves along (e.g., spatially intersects) the centerline 104, a graphical proxy marker 114 is generated (e.g., by output generator 20) based on the pointer location with respect to the centerline 104 (e.g., provided by proxy marker data 42 in response to position calculator 36 determining the pointer position coinciding with the centerline).

In this example, the graphical proxy marker 114 has a toroidal shape having a center co-located with a nearest given geometric knot along the centerline. For example, the graphical proxy marker is oriented to lie in a plane that is orthogonal to a direction of the centerline at the given geometric knot. As the pointer 110 moves along the centerline 104 (e.g., along direction 112), the position of the proxy marker 114 would change based on the determined location of the pointer with respect to the centerline. Thus, as pointer 110 moves along centerline 104, the position of the proxy marker 114 will change accordingly. In some examples, the size and/or orientation of the proxy marker also can vary such as disclosed herein.

As shown in the example of FIG. 4, a fixed location along centerline 104 is selected in response to a user input (e.g., by user input device 16). In response to setting the location, a graphical attribute of the marker can change to indicate that the location is set. In the examples of FIGS. 3 and 4, this is demonstrated as changing from a dashed line to a solid line. In other examples, the color and/or brightness of the marker that is displayed in the GUI 100 can change to indicate that the marker location has been set. After one or more marker locations have been set with respect to the desired anatomic structures (e.g., centerline), final marker data (e.g., data 44) can be stored in memory for use in rendering the graphical representation of the final graphical marker at the selected fixed location relative to the anatomic structure.

Figure 5:
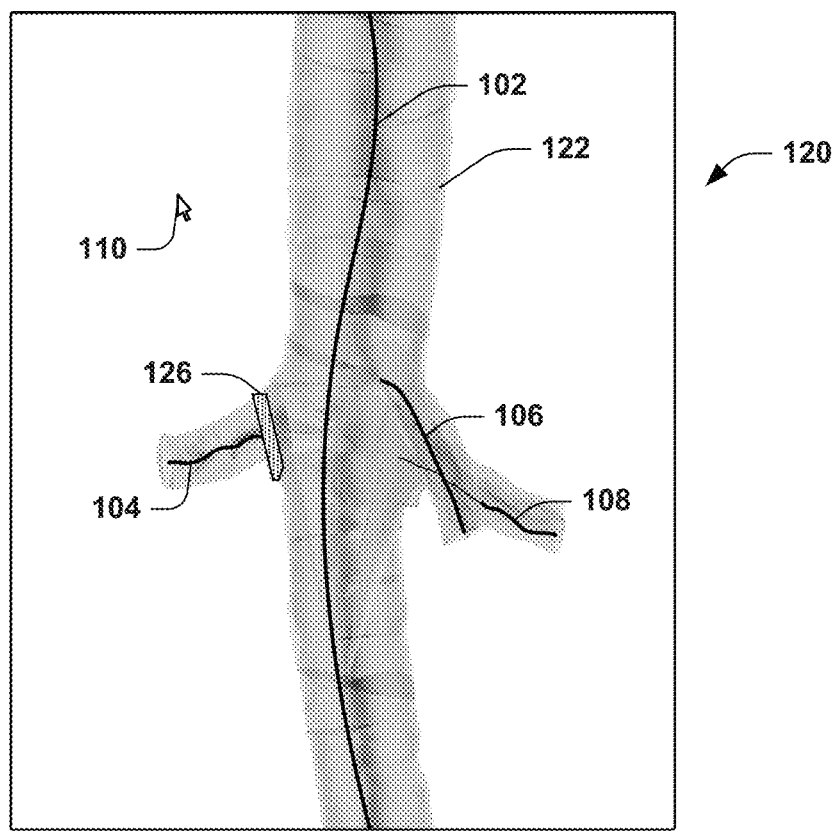
FIG. 5 depicts an example of an output visualization showing an anatomic structure with a final graphical marker at a selected location.
Figure 6:
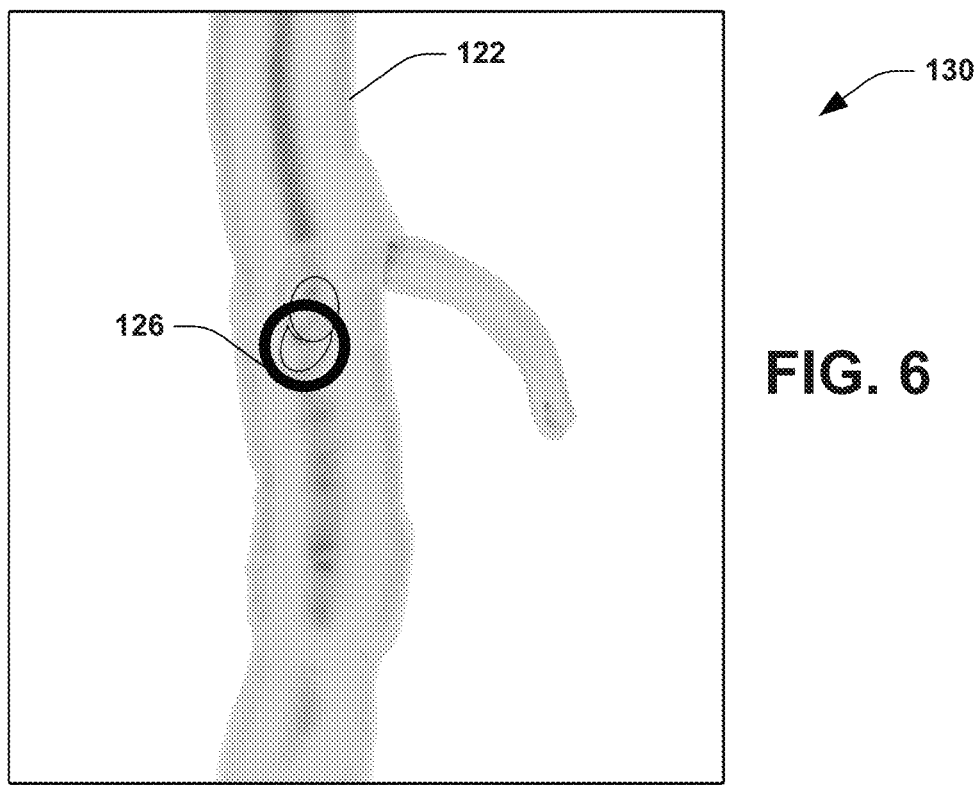
FIG. 6 depicts the anatomic structure of FIG. 5 showing an example of another view of the anatomic structure, looking through an ostium into the aorta, with the final graphical marker at the selected location of the final graphical marker.
Figure 7:
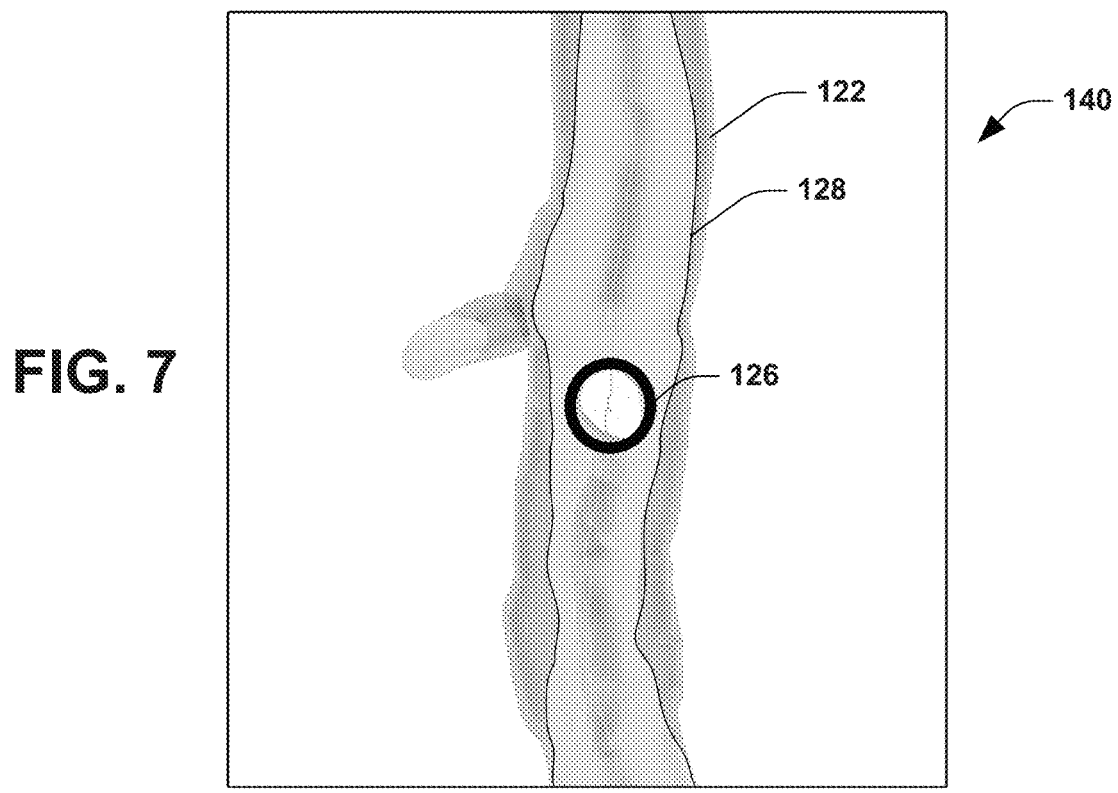
FIG. 7 depicts the anatomic structure of FIG. 5 showing an example of another view of the anatomic structure, a cut-away view thereof looking from the aorta into the ostium, with the final graphical marker at the selected location.

FIGS. 5-7 demonstrate output visualizations 120 for a plurality of different views for the same portion of the descending aorta shown in FIGS. 2-4. In this example, the visualization 120 depicts an outer surface of the descending aorta 122 (e.g., generated by rendering method 22 based on surface model data 46). Also demonstrated in the visualization 120 are centerlines 102, 104, 106 and 108 for the aorta and the branch arteries (e.g., generated by rendering method 22 based on centerline model data 38). The visualization 120 also includes a graphical representation of the final graphical marker shown at 126. The shape of the graphical marker 126 in the output visualization 120 is different from the proxy marker 114 shown in FIGS. 3 and 4.

As demonstrated in FIG. 5, showing a side perspective view of the marker 126, the shape and cross-sectional configuration of the marker 126 is defined by the shape and cross-sectional dimension of the branch artery (e.g., derived based on the surface model data 46). For example, a predetermined toroidal shape for the proxy marker 114 may be used for setting the location and when the visualization of the anatomic structure is generated, such as shown in FIG. 5, the final marker can be generated at the fixed location according to the cross-sectional shape of the surface at the centroid location for such geometric knot. For example, the final marker 126 can be a three-dimensional ring having a short cylindrical sidewall and a radius at each end thereof that is based on the radius of the tubular anatomic structure at the geometric knot where the marker has been placed. The axial ends of the marker may be circular or have non-circular, anatomic contours defined by the model data 46, which can be lofted by interpolating between the respective contours (e.g., by lofting with Bezier curves). The final marker can be rendered in a different color from the surface of the anatomic structure (e.g., red and blue, respectively), which color can remain the same among difference views. The final marker can also be provided a radial thickness (e.g., a number of voxels thick) to at least approximate the thickness of the vessel wall, such as shown in the views of FIGS. 6 and 7. Thus, the shape of the marker 126 is configured to conform to the shape of the surface of the vessel wall.

With reference back to FIG. 1, the rendering method 22 may be programmed to generate the surface of the tubular anatomic structure as a lofted surface. For example, at each geometric knot of the centerline a given number of unit vectors are created perpendicular to the tangent line of the control point, such as by creating an orthonormal basis. Each vector direction extends outwards until the voxel values drop below a threshold. The length of each vector may be set vary according to the radius of the vessel surface being created at each centroid location. Such as may be generated from a spline at the selected geometric knot.

In an example, the final graphical marker 126 may also be generated (e.g., by rendering method as a lofted surface. As discussed with respect to FIG. 1, the marker 126 is visible with respect to the anatomic structure being visualized from multiple different views. In each of the views, the marker will be positioned at the same location as provided in the final marker data 44 (e.g., linked to a geometric knot along the centerline). In the examples of FIGS. 5, 6 and 7, the reference marker 126 is placed at the user selected location to identify an ostium between a branch artery and the main descending aorta 122.

FIG. 6 demonstrates an example of an output visualization 130 looking into the descending aorta through the ostium represented at the marker 126. FIG. 7 illustrates a cut-away view of the descending aorta exposing the ostium viewed axially (e.g., along the branch centerline) into the branch artery and showing the location of the marker 126 with respect to the branch artery. The cut-away view of FIG. 7 also shows an interior sidewall 128 of the aorta. Each of the different views shown in FIGS. 5, 6 and 7, for example, may be selected by implementing display controls 24 in response to user input data from the user input device. Additionally, in some examples, multiple views may be displayed concurrently in one output device (e.g., in a plurality of windows) or in a plurality of such output devices 18.

Figure 8:
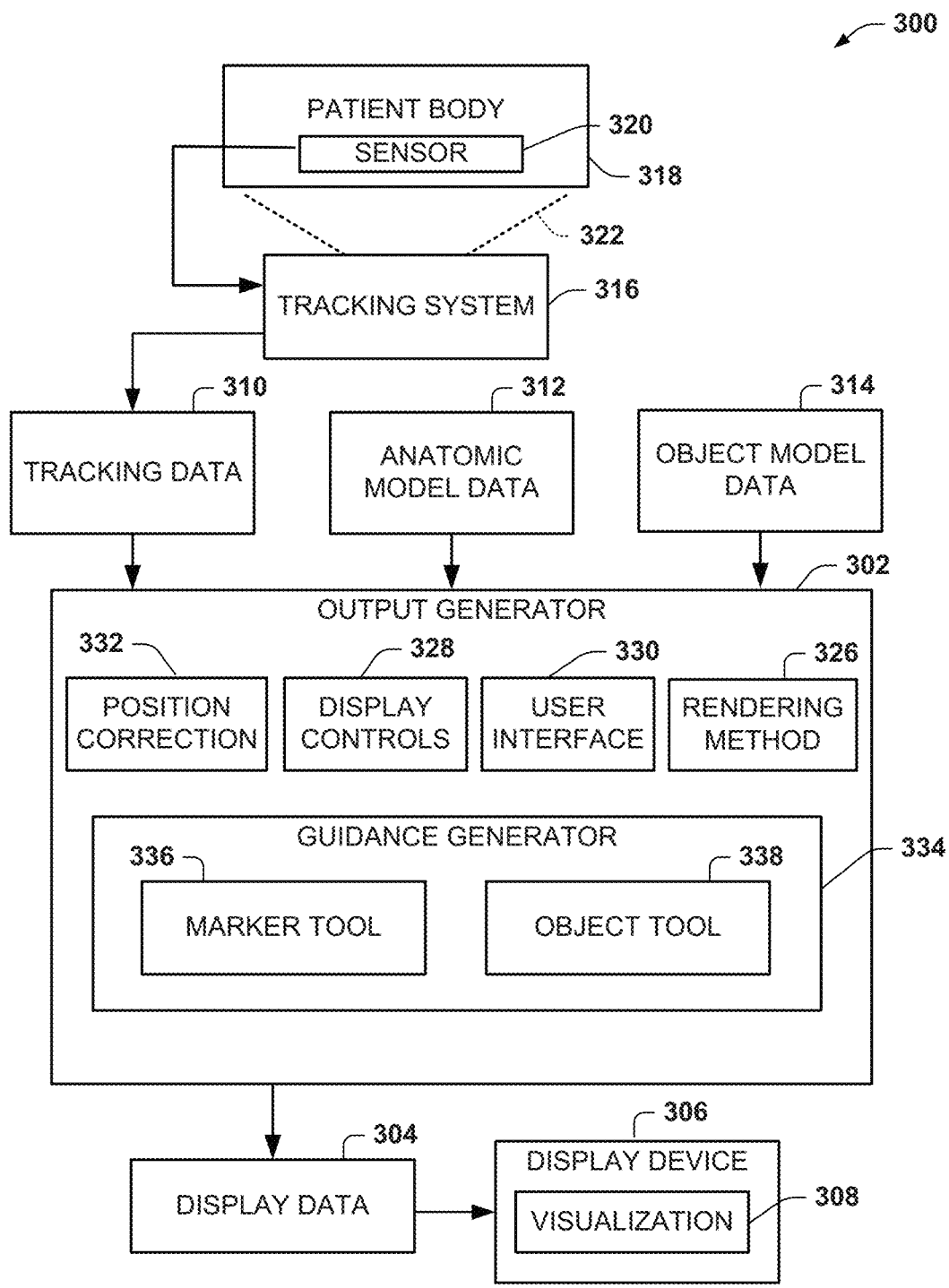
FIG. 8 depicts an example of an intra-operative guidance and visualization system.

FIG. 8 depicts an example of a visualization system 300 that includes an output generator 302 programmed to generate visualization data 304, which can be provided to a display to render a corresponding graphical representation. The output generator 302 can generate the visualization data 304 that is provided to a display device 306 for displaying a corresponding visualization 308. The visualization 308 can provide intra-operative guidance such as for surgical navigation, which can include one or more graphical markers as disclosed herein. The output generator 302 can generate the visualization data 304 based on tracking data 310, anatomic model data 312 and object model data 314. The anatomic model data 312 can be a patient-specific implicit model that describes one or more anatomic structures in three-dimensional space (e.g., corresponding to the centerline and surface model data 38 and 46 of FIG. 1).

The object model data 314 can correspond to another three-dimensional implicit model that has been generated to describe geometry of an instrument (e.g., a catheter and/or guidewire) that is being inserted into the patient during a procedure. For example, the object model data 314 can correspond to an analytical or parametric representation of a surgical instrument, which may be a generally rigid surgical instrument or an articulated instrument that includes a flexible tip such as wires, catheters and the like. Accordingly, the complexity of the model data 314 and the corresponding implicit model that it defines can vary according to the type of instrument or other object that is being tracked within the patient's anatomy. In addition to parameterizing the geometry of the object, the object model data 314 can also be configured to model other properties of the object (e.g., resilience and/or ductility).

The system 300 can include a tracking system 316 that includes one or more sensors 320 can be affixed to or integrated into the instrument to enable tracking of its location by the tracking system. The tracking system 316 is configured to generate the tracking data 310, which is registered in a common three-dimensional coordinate system with the anatomic model data 312 and the object model data 314 to enable real-time tracking. The common coordinate system can represent a coordinate system for image data that has been acquired preoperatively relative to the tracking data that is generated intra-operatively by the tracking system 316.

For example, the tracking system 316 can include a transmitter (e.g., an electromagnetic field generator) that provides a non-ionizing field, demonstrated at 322, which is detected by each sensor 320 to provide a corresponding sensor signal to the tracking system. An example tracking system 316 is commercially available from Northern Digital, Inc., of Ontario, Canada. The tracking system 316 can provide the tracking data 310 at an output sample rate (e.g., sixty samples per second) sufficient to enable substantially real time determination of sensor location (e.g., to provide a vector describing sensor position and orientation). A tracking processing subsystem (not shown) thus can process each frame of tracking data 310 such that the registered tracking data can likewise represent real time tracking data acquired by the tracking system 316 that can be registered into the coordinate system of the anatomic model and rendered as a graphical representation, as disclosed herein. The tracking system 154 can provide the tracking data with an output sample rate to enable computation of real time positioning and generation of the visualization 308 to include the object to which the sensor is attached.

As a further example, the output generator 302 includes a registration matrix that is programmed to convert the tracking data 310 from a coordinate system of the tracking system 316 to a coordinate system that is common for the model data 312 and 314. The common coordinate system may be a spatial coordinate system of a patient or coordinate system of a pre-operative image that is used to generate the anatomic model. The tracking system 316 may generate the tracking data 310 as a plurality of frames and the registration matrix may be applied to convert each of the plurality of frames of the tracking data into a coordinate system to enable processing of the tracking data and the model data 312 and 314 in a common coordinate system.

The output generator 302 includes a rendering method 326 programmed to produce a three-dimensional plot corresponding to the visualization data 304 based on the input data 310, 312 and 314. Various types of rendering software (e.g., commercially available or proprietary) can be utilized and implemented as the rendering method 326 and can vary according to the type of models generated for use by the system 300.

The output generator 302 can also include display controls 328 that can control the output that is provided intra-operatively. The display controls 328 can be configured to selectively generate any number of one or more displays concurrently on one or more display devices 306, each of which can include a different view of the object and the anatomic structure. The respective views can be selected automatically such as by default parameters or it can be adjusted in response to the user input just as can be provided a user interface 330. This display controls 328 can further control a viewing angle for each of the visualizations of the anatomic model and the object that are presented to the user. Since the structures in each visualization are virtual renderings based on implicit models, the output visualization is not constrained to any particular viewing angle or type of visualization.

In some examples, the display controls 328 can compute and display task-specific visualizations, such as may include an optimal view for a particular task (for example, cannulating a renal artery). For example, when cannulating a vessel, it is useful to visualize the vessel and wire without distractions or obstructions. The output generator 302 is able to create this visualization since each graphical marker, each vessel and each device are virtual renderings generated by the rendering method 326. Additionally, because each the models 312 and 314 are easily separated into its constituent parts, other items can be effectively removed from the display and only show the clinician the pertinent geometry and telemetry for the current task.

The rendering method 326 can correspond to the rendering method 22 of FIG. 1. By way of example, the rendering method 322 includes a centerline render function programmed to plot a centerline of the anatomic structure based on the anatomic model data 312, which includes parameters describing the geometry of the anatomic structure (e.g., an elongated curved tubular structure, such as a vessel or intestine). As mentioned, the anatomic model data 312 can include a single parameter to describe the centerlines (e.g., geometric knots) that can be evaluated to form a spline curve. As an example, the centerline render function 318 can compute the centerline as a function of a single parameter (u) that goes from zero to one and varies along a path corresponding to the axis of the tubular structure taken by selecting a spacing of the parameter u.

The rendering method 326 can also include a surface render function that can produce a plot for a surface of the anatomic structure based on the implicit surface model defined by the model data 308. As an example, the rendering method 326 can compute the surface as a function of two variables, such as the variable u, which extends along the centerline of the tubular structure and another parameter (v) which varies as one travels tangentially around the surface. As disclosed herein, the anatomic model data 312 can store the surface information as a series of slices in which each slice can be represented by a series of geometric knots of an elongated tubular structure. The surface render function can create vectors perpendicular to the tangent line of the control point at each geometric knot unit vectors, which vectors can have a radius corresponding to surface points defined by radius of the anatomic structure at such point. The surface render function can visualize the surface by evaluating the parameters to generate polygons (e.g., triangles) that tessellate the surface. Such polygons can be rendered efficiently with various computer graphics, hardware and software.

The rendering method 326 can also include an object render function to render a graphical representation of the object based on the object model data 314 and the tracking data 310, which is registered in a common coordinate system with the anatomic model data. The registered tracking data 306 represents a position and orientation of one or more sensors in three-dimensional space corresponding to the same coordinate system in which the anatomic model has been registered. The object render function can be programmed to generate a graphical representation for each object depending on the location of the object defined by the tracking data 310. By way of example, the object render function can plot rigid objects (and parts of objects that are rigid) by applying a transformation matrix multiplied by the overall registration matrix. For the case of articulated objects (e.g., instruments with a flexible tip, such as wires and catheters), the object render function can be programmed to plot different parts of the structure separately. As an example, the object render function can render an elongated instrument in discrete parts.

The output generator 302 can also include a guidance generator 334 programmed to generate user perceptible guidance that can be included in the visualization data 304 and presented in the visualization 308. Some guidance can be static whereas other guidance can be dynamic. For example, the guidance generator 334 can include a marker tool 336 programmed to place a graphical marker at a user-selected location with respect to an anatomic structure. The marker tool 336 can correspond to the marker tool 30 of FIG. 1.

By way of example, the marker tool 336 may be activated in response to a user input of through the user interface 330. The marker tool 336 can be programmed to display a graphical representation of a virtual anatomic reference structure, such as a centerline. The marker tool can further be programmed to determine a location parameter for the marker along the centerline (or other reference) in response to a first user input from the user input device. The location parameter may be derived by hovering a pointer of the user interface 330 over the graphical representation of the centerline. The rendering method 326 may generate the visualization data 304 to display a graphical proxy marker based on the location parameter. For example, the graphical proxy marker may be a toroidal object circumscribing the graphical representation of centerline. The placement of the proxy marker can be adjusted as the pointer moves along the centerline. A fixed location along the centerline for a final graphical marker may then be selected in response to a user input from the from the user interface 330, such as disclosed herein. The fixed location can be stored in memory associated with a respective point along the centerline (e.g., geometric knot of a centerline model). The marker tool may be closed and corresponding visualization data 304 be generated to includes a visualization of the anatomic structure and a graphical representation of the final graphical marker at the selected anatomic location of the structure. If the tracking system is operating and the sensor is within the anatomic structure, the output generator can also include a graphical representation of the object in the visualization (see, e.g., FIG. 9).

In some examples, the guidance generator 334 also includes an object tool 338 programmed to provide graphical guidance with respect to an object (e.g., guidewire, catheter and/or other instrument) that is rendered in the visualization based on the tracking data and the object model data. For example, object tool 338 provides guidance relating to the position and/or trajectory path of the object and the spatial position (three-dimensional spatial position) of one or more anatomic features or graphical marker. As mentioned, the graphical marker may be placed at a waypoint or target site. As an example, a distance calculator can determine a spatial distance between a selected feature (e.g., graphical marker or anatomic landmark) and a point along the object (e.g., corresponding to a distal tip of an instrument or other predetermined location along the object). The guidance generator 334 can provide a visual indicator, an audible indicator or a combination of audible and visual indicators based on the distance. For example, an audible indicator can provide a series of beeps or tones that increase in frequency as a function of decreasing distance between the object and the location of the target feature. The guidance generator 334 can specify a color code to be applied to the graphical marker or other selected feature of the output visualization, such as green to indicate that the position is on target, yellow to indicate a deviation within a predetermined parameter or red to indicate that the position is outside of expected parameters.

As a further example, the guidance generator 334 can also include a directional indicator that can produce virtualized graphical indictor, such as to show a direction that a distal tip of the object (e.g., a catheter or wire) is oriented. The graphical indicator can be rendered as a series of short lines translated along a given sensors positive Z axis. The visual indicator thus can provide an easy way to determine whether the object is aligned with a given part of the anatomic structure (e.g., as specified by a graphical marker) to facilitate advancing the object (e.g., catheter and/or guidewire) through or into a graphical marker that has been positioned at an ostium of a target branch vessel. As mentioned above, the appearance of the graphical marker and other guidance visualization further will vary depending on the particular viewing angle that is being produced.

The guidance generator 334 can also provide information to graphically differentiate anatomic locations or other target sites, such as by using different color codes for different structures of interest. For example, the graphical marker can be rendered as a thick (e.g., multi-voxel thick) ring or cylindrical body residing at a selected location (e.g., ostium waypoint or target location). The guidance generator 334 can provide additional feedback to the user. For example, when the tip of the object gets within a predetermined distance of an ostium, which has been indicated by a graphical marker placed at such location, as disclosed herein, the guidance generator 334 can change colors (and/or brightness) of the graphical marker in each view as the tip is determined to be within a predetermined spatial distance of the graphical marker.

Figure 9:
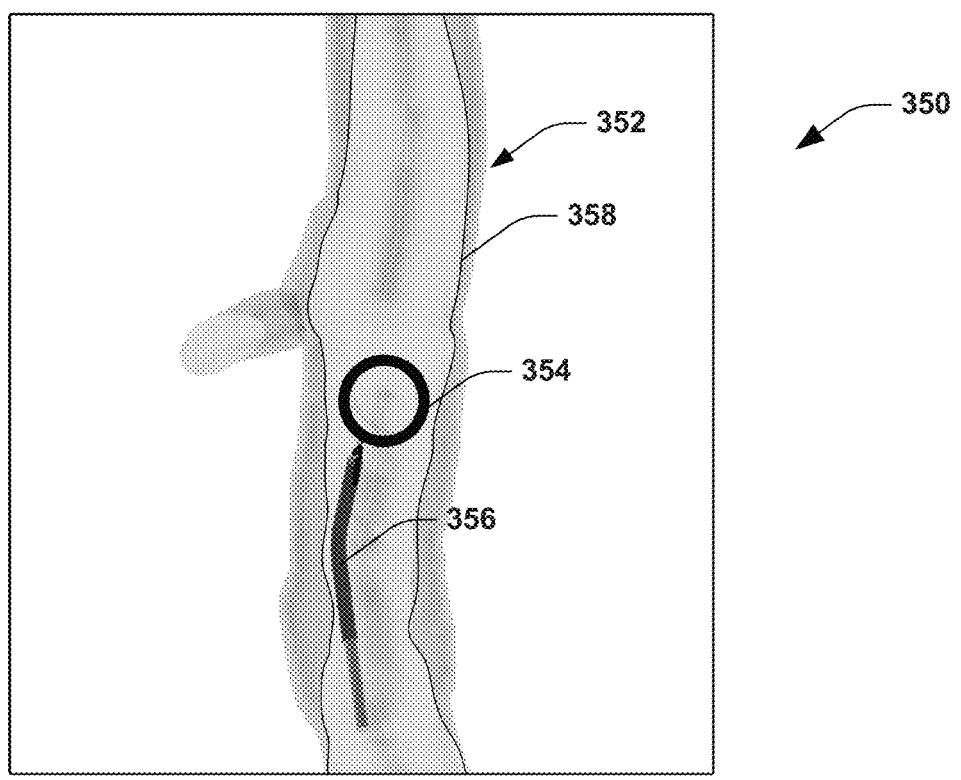
FIG. 9 depicts an example of an output visualization that can be generated by the system of FIG. 8.

FIG. 9 depicts an example of an output visualization 350 that can be generated by the output generator 302 (also corresponding to output generator 20 of FIG. 1) based on the tracking data 310, the anatomic model data 312 and the object model data 314. In the example of FIG. 9, the output visualization 350 is a cut-away view (similar to FIG. 7) that includes a graphical representation of the anatomic structure 352 (e.g., the descending aorta) as well as the graphical marker 354 and a graphical representation of an instrument 356. As described above, the graphical marker 354 is placed at a user-selected position (e.g., using marker tool 30, 336) to facilitate intra-operative position of an actual physical surgical instrument that is graphically represented by 356 (e.g., generated by output generator 20, 302). That is, the position of the instrument 356 with respect to the anatomic structure 352 and graphical marker 354 in the visualization 350 varies over time based on tracking data 310 that is registered into the same coordinate system as the data used to produce the visualization of the anatomic structure 352 and graphical marker 354.

Figure 10:
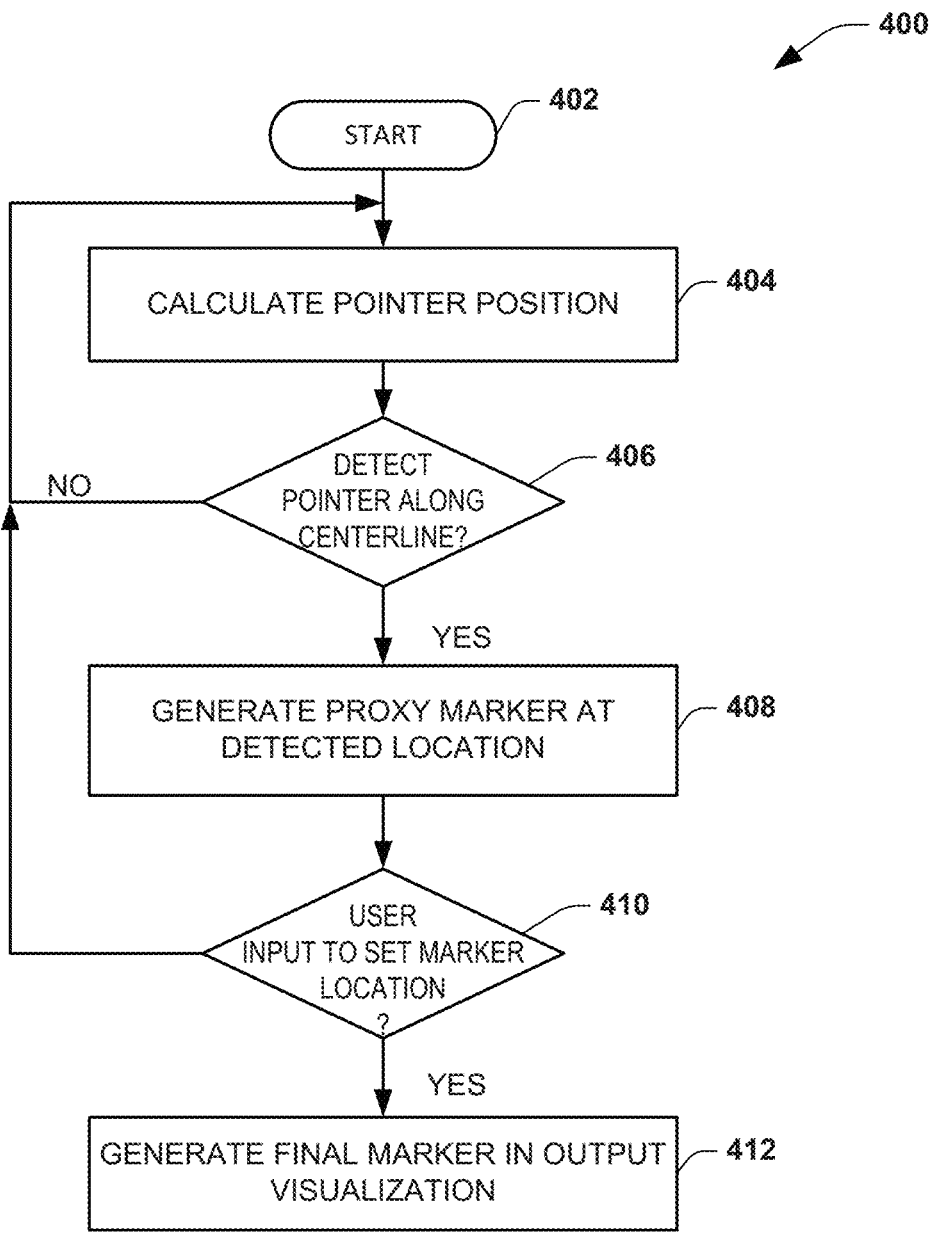
FIG. 10 is a flow diagram depicting an example of a method to mark anatomic structures.

In view of the foregoing structural and functional features described above, methods that can be implemented will be better appreciated with reference to FIG. 10. While, for purposes of simplicity of explanation, the method of FIG. 10 is shown and described as executing serially, they are not to be limited by the illustrated order, as the methods could occur in different orders and/or concurrently with other aspects from that shown and described herein. Moreover, not all illustrated features may be required to implement a method. The methods or portions thereof can be implemented as instructions stored in one or more non-transitory storage media as well as be executed by a processor of a computer device or special purpose computer device (e.g., a dedicated computer or workstation) to access data sources and perform the functions disclosed herein, for example.

FIG. 10 depicts a flow diagram of a method 400 that can be utilized to place one or more reference markers with respect to anatomic structures. The method 400 begins at 402 such as in connection with activating a marker tool (e.g., marker tool 30, 336) of a visualization system (e.g., system 10, 300). The method 400 can implemented in conjunction with a computer system that includes a user input device (e.g., user input device 16 or interface 330) such as disclosed herein.

At 404, a position of a pointer is calculated. For example, the position may be calculated in response to user input data from an input device. The position can be spatial coordinates in a visualization that also includes a graphical representation of an anatomic reference of an anatomic structure. For example, the anatomic reference may be a centerline or an axis of symmetry, which may vary depending upon the shape and size of the anatomic structure being visualized. In an example, the pointer position may be calculated by a position calculator 36 or provide as part of user input data from the user interface associated with the input device.

At 406, a determination is made as to whether the pointer is detected along the reference (e.g., centerline). For example, the determination may be made by position calculator 36 by comparing spatial coordinates of the pointer and the graphical representation of the anatomic reference (e.g., centerline) that is rendered in the visualization. If the pointer is not detected to be along the reference, the method returns to 404 to continue monitoring the relative position between the pointer and the visualized reference. If the pointer is detected along the centerline at 406, method proceeds to 408. Additionally, in response to detecting the pointer along the centerline, the location (e.g., spatial coordinates in the visualization) of the pointer on the centerline may be stored in memory, which may be linked to a nearest given point along the reference structure (e.g., a geometric knot). At 408, a proxy marker is generated (e.g., by marker generator 32) at the detected location. For example, the location can correspond to a nearest geometric knot of the reference structure.

At 410, a determination is made as to whether a user input has set the marker location. For example, the marker location may be set in response to a user input with a user input device (e.g., clicking on the proxy marker or selecting a button). If no user input is received to set the location, the method returns to 404 to continue and repeat the process in which the proxy marker may be generated and visualized with respect to the reference structure of the marker tool as the pointer moves along the reference structure. In response to a user input setting the marker location at 410, the method proceeds to 412 to generate an output visualization that includes a final marker in the output visualization, such as disclosed herein (see, e.g., FIGS. 3-7 and 9). For example, the output visualization can be generated (e.g., by output generator 20 of FIG. 1 or generator 302 of FIG. 8) to represent a location of the final graphical marker at the user-selected location relative to the geometry of the anatomic structure. In some examples, the output visualization can include a graphical representation of an instrument generated in substantially real time based on tracking data from one or more sensors to facilitate positioning and guidance of the instrument. The output visualization can include any number of concurrently generated views, which can be modified (e.g., in response to a user input), such as disclosed herein. Each view can further include the graphical marker or the marker may be hidden in response to another user input.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in one or more non-transitory machine-readable media), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions that implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of components or methods, as further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, the term "including" means including but not limited to. The term "based on" means based at least in part on.

What is claimed is:

1. One or more non-transitory computer readable media having instructions stored thereon, for execution by a computer that includes a graphical user interface, the instructions to perform a method comprising:
    displaying a graphical representation of an anatomic structure on the graphical user interface based on model data, the model data describing a geometry of the anatomic structure including geometric knots distributed at respective positions along a centerline of the graphical representation of the anatomic structure;
    determining a location parameter for a graphical marker on the graphical user interface along the graphical representation of the anatomic structure based on a given position of a given geometric knot of the geometric knots;
    displaying the graphical marker on the graphical representation of the anatomic structure on the graphical user interface based on the location parameter;
    changing the location parameter to move the graphical marker along the graphical representation of the anatomic structure based on a user input at a user input device, wherein the location parameter for the graphical marker is determined based on a closest geometric knot of the geometric knots relative to the graphical marker as the graphical marker is moved along the graphical representation of the anatomic structure, and wherein the graphical marker has a size parameter and a shape parameter, at least one of the size and shape parameters varying as a pointer of the user input device moves along the along the graphical representation of the anatomic structure to change the location parameter for the graphical marker;
    selecting a fixed location along the graphical representation of the anatomic structure for the graphical marker to fix the graphical marker relative to the graphical representation of the anatomic structure, the fixed location corresponding to a position of a geometric knot of the geometric knots; and
    generating an output visualization that includes at least one view of the graphical representation of the anatomic structure and a graphical representation of the graphical marker at the fixed location based on the position of the geometric knot.

2. The media of claim 1, wherein the user input comprises hovering a pointer of the user input device over the graphical representation of the anatomic structure.

3. The media of claim 1, wherein at least one of the size and shape parameters vary based on the location parameter according to a cross-sectional dimension of the graphical representation of the anatomic structure.

4. The media of claim 1, wherein the geometry of the anatomic structure includes a tubular portion represented by a patient-specific implicit model that includes centerline model data and surface model data derived from imaging data acquired for the tubular portion of the anatomic structure.

5. The media of claim 1, wherein generating the output visualization further comprises generating a graphical representation of a catheter or guidewire within the at least one view of the anatomic structure based on tracking data for at least one sensor located within the anatomic structure and varies with respect to time according to a relative position of the at least one sensor within the anatomic structure.

6. The media of claim 1, wherein the anatomic structure comprises an elongated blood vessel that includes at least one branch vessel, the fixed location specifying a user-selected location of an ostium for the at least one branch vessel.

7. A computer-implemented method for marking an anatomic structure, comprising:
  displaying a graphical representation of the anatomic structure on an output device based on model data, the model data describing a geometry of the anatomic structure including geometric knots distributed at respective positions along a centerline of the graphical representation of the anatomic structure;
  determining a location parameter for a graphical marker with respect to the graphical representation of the anatomic structure based on a given position of a given geometric knot of the geometric knots;
  displaying the graphical marker on the graphical representation of the anatomic structure based on the location parameter;
  changing the location parameter to move the graphical marker along the graphical representation of the anatomic structure responsive to moving a pointer of a user input device along the graphical representation of the anatomic structure, wherein the location parameter for the graphical marker is determined based on a closest geometric knot of the geometric knots relative to the graphical marker as the graphical marker is moved along the graphical representation of the anatomic structure, and wherein at least one of a size parameter and shape parameter of the graphical marker varies as the pointer of the user input device moves along the graphical representation of the anatomic structure based on the location parameter;
  selecting a fixed location along the graphical representation of the anatomic structure for the graphical marker to fix the graphical marker relative to the graphical representation of the anatomic structure, the fixed location corresponding to a position of a geometric knot of the geometric knots; and
  generating an output visualization that includes at least one view of the graphical representation of the anatomic structure and a graphical representation of the graphical marker at the fixed location based on the position of the geometric knot.

8. The computer-implemented method of claim 7, wherein the location parameter for the graphical marker is determined based on the closest geometric knot and the closest geometric knot is determined based on a position of the pointer relative to a subset of geometric knots of the geometric knots.

9. The computer-implemented method of claim 8, wherein the at least one of the size and shape parameters further varies based on a cross-sectional dimension of the graphical representation of the anatomic structure.

10. The computer-implemented method of claim 8, wherein at least one of a size parameter and shape parameter of the graphical marker at the fixed location is set based on the geometry of the anatomic structure.

11. The computer-implemented method of claim 7, wherein one of:
  the graphical representation of the anatomic structure comprises a graphical representation of the centerline of the anatomic structure, and wherein the graphical marker comprises a toroidal shape having a center, the centerline extending through the center of the toroidal shape of the graphical marker as the graphical marker moves along the graphical representation of the anatomic structure and is fixed at the fixed location; and the graphical representation of the anatomic structure comprises a graphical representation of the centerline of the anatomic structure, and wherein the centerline comprises a curved portion, the graphical marker having a center positioned along the curved portion of the centerline, the graphical marker being oriented substantially perpendicular to the centerline.

12. The computer-implemented method of claim 7, wherein the geometry of the anatomic structure includes a tubular portion, the model data including a patient-specific implicit model describing a geometry of the tubular portion of the anatomic structure, the patient-specific implicit model including centerline model data characterizing the centerline and surface model data derived from imaging data acquired for the anatomic structure.

13. The computer-implemented method of claim 7, wherein the anatomic structure comprises an elongated blood vessel that includes at least one branch vessel, the fixed location specifying a user-selected location of an ostium from the at least one branch vessel, and
  wherein generating the output visualization further comprises generating a graphical representation of a catheter or a guidewire within the at least one view of the elongated blood vessel based on tracking data for at least one sensor located within the anatomic structure and varies with respect to time according to a relative position of the at least one sensor within the anatomic structure.

14. The computer-implemented method of claim 7, further comprising determining an orientation of the graphical marker with respect to the centerline as the graphical marker is moved along the graphical representation of the anatomic structure based on the position of the graphical marker relative to the closest geometric knot, such that the graphical marker is rendered in the graphical representation with the determined orientation.

15. A system for marking an anatomic structure, the system comprising:
  a non-transitory computer-readable medium configured to store data and instructions, the data comprising model data describing a geometry of the anatomic structure including geometric knots distributed at respective positions along a centerline of a graphical representation of the anatomic structure;
  a processor configured to access the non-transitory computer-readable medium and execute the instructions, the instructions comprising:
    an output generator programmed to generate an output visualization that includes at least one view of the graphical representation of the anatomic structure based on the model data, and a graphical representation of a graphical marker at a fixed location on the graphical representation of the anatomic structure based on a position of a geometric knot of the geometric knots;
    a marker generator programmed to:
      determine a location parameter for the graphical marker along the graphical representation of the anatomic structure based on a given position of a given geometric knot of the geometric knots, wherein the location parameter for the graphical marker is determined based on a closest geometric knot of the geometric knots relative to the graphical marker as the graphical marker is moved along the graphical representation of the anatomic structure, wherein the graphical marker has a size parameter and a shape parameter, at least one of the size and shape parameters varying as the graphical marker is moved along the along the graphical representation of the anatomic structure; and select the fixed location along the graphical representation of the anatomic structure for the graphical marker to fix the graphical marker relative to the graphical representation of the anatomic structure, the fixed location corresponding to the position of the geometric knot of the geometric knots.

16. The system of claim 15, further comprising a user input device, wherein the location parameter for the graphical marker changes as a pointer of the user input device moves along the graphical representation of the anatomic structure based on a user input, and wherein the marker generator is programmed to identify the closest geometric knot of the geometric knots based on a position of the pointer relative to a subset of geometric knots of the geometric knots.

17. The system of claim 16, wherein the output visualization further comprises a graphical representation of a catheter or guidewire within the at least one view of the anatomic structure based on tracking data for at least one sensor located within the anatomic structure and varies with respect to time according to a relative position of the at least one sensor within the anatomic structure.

\* \* \* \* \*